United States Patent [19]
Todd

[11] Patent Number: 5,630,820
[45] Date of Patent: May 20, 1997

[54] SURGICAL BICOMPARTMENTAL TENSIOMETER FOR REVISION KNEE SURGERY

[75] Inventor: Ronald C. Todd, Austin, Tex.

[73] Assignee: Sulzer Orthopedics Inc., Austin, Tex.

[21] Appl. No.: 349,447

[22] Filed: Dec. 5, 1994

[51] Int. Cl.⁶ ................................................ A61B 17/56
[52] U.S. Cl. ........................................ 606/90; 606/102
[58] Field of Search ................... 606/90, 88, 87, 606/36, 96, 102, 105; 600/201, 202, 214, 215, 219, 222

[56] References Cited

U.S. PATENT DOCUMENTS

| | | | |
|---|---|---|---|
| 4,501,266 | 2/1985 | McDaniel | 606/90 X |
| 4,938,230 | 7/1990 | Machek et al. | 128/777 |
| 5,116,338 | 5/1992 | Poggie et al. | 606/90 |
| 5,213,112 | 5/1993 | Niwa et al. | 128/774 |
| 5,431,653 | 7/1995 | Callaway | 606/90 |
| 5,468,244 | 11/1995 | Attfield et al. | 606/90 |

OTHER PUBLICATIONS

"Your Partner" Protek A.G. 1991, pp. 159, 163.
"F/S Modular Total Knee Replacement System" Protek A.G., Jan. 1991, pp. 19–21, 45, 49.

Primary Examiner—Guy V. Tucker
Attorney, Agent, or Firm—John R. Merkling

[57] ABSTRACT

A bicompartmental tensiometer for use in prosthetic knee surgery, and in particular for use in revision knee surgery. The tensiometer comprises two parallel, independently operable jaws which are inserted between resected surfaces on the distal femur and the proximal tibia. The jaws are opened manually by the surgeon until the proper tension is placed on the collateral ligaments. Each of the jaws comprises two paddles which remain parallel to each other as they are opened. Moreover, the two jaws remain parallel to each other, or in the same angular orientation, when adjusted to be placed adjacent the condyles. Each jaw is held open by a pawl which engages a rack.

13 Claims, 2 Drawing Sheets

SURGICAL BICOMPARTMENTAL TENSIOMETER FOR REVISION KNEE SURGERY

FIELD OF MY INVENTION

My invention relates to surgical apparatus, and specifically to apparatus for use in knee surgery, and more specifically to apparatus, for placing the medial and lateral collateral ligaments of the knee in tension, for the purpose of balancing those ligaments during surgical implantation of a prosthetic knee.

BACKGROUND OF MY INVENTION

When human joints, such as the knee, become diseased or otherwise are incapable of functioning, surgical intervention is possible. Surgeons expose the junction between the tibia and the femur, temporarily disconnect the patella, resect away parts of the femur or tibia or both, and replace the ends of the femur and tibia with artificial prostheses. Orthopedic implants for the human knee generally have a femoral and tibial component. The tibial component is usually placed on the resected proximal surface of the tibia and frequently has a metal base plate with a shaft extending into the medullar canal. The base plate usually carries an ultra high molecular weight polyethylene (UHMWPE) articulating surface. The articulating surface has medial and lateral condyle compartments, approximating the medial and lateral condyle compartments of a natural tibia in form and function. A femoral component is implanted on a resected distal end of the femur and presents artificial condyles, similar in form and function to the natural condyles of the femur which have been cut away, which articulate with the condyle compartments of the tibial component. A femoral component generally comprises the condyle articulating surfaces and fixation means, which may include an elongated stem extending into the medullar canal of the patient. Such prostheses are well known and examples can be found in U.S. Pat. Nos. 4,963,152; 5,062,852; and 5,071,438.

For patients who require an artificial knee prothesis, degeneration of the bone at either the tibia or femur or both may be occurring. Moreover, this degeneration may be proceeding unevenly with respect to the two condyles, or the two condyle compartments. A side effect of this degeneration is that the anatomic alignment of the femur to the tibia may become disjointed causing an imbalance to the collateral ligaments. It is known that some patients require a re-operation and the installation which is called a "revision" knee prosthesis. The revision knee prosthesis is generally more massive than a so-called "primary" knee prosthesis. The revision femoral knee condylar parts may be thicker and more robust and the medullar shaft may be substantially longer. Moreover, in many cases, degeneration of one condyle may be substantially more advanced than the other.

Whether natural or prosthetic, the knee joint is supported by the patella and by ligaments, including the medial and lateral collateral ligaments on either side of the knee, and the cruciate ligaments behind the knee. If present, these ligaments, particularly the collateral ligaments, must be under proper tension, and balance, both when the knee is in extension and when it is in flexion, in order to maintain correct anatomic alignment. It is important, therefore, for a surgeon performing knee replacement surgery to be able to size the prosthesis and place resection cuts appropriately so that the reassembled knee will cooperate with the ligaments to form a stable joint. This is particularly problematic in the case of revision surgeries, where substantial changes in the bone structure, and also changes in the balance of the medial and lateral collateral ligaments may be expected.

In the past, surgeons have placed the exposed knee joint under tension both in extension and flexion either manually, or by use of instruments. There remains a need, however, for instrumentation which can enable the surgeon to spread the joint between the distal femur and the proximal tibia, placing the collateral ligaments in tension, both when the knee is in flexion and in extension in an effort to establish the balance of these ligaments with respect to the correct, or corrected, anatomic alignment of the knee joint. Moreover, such apparatus is needed which would operate on both condyles simultaneously to place the medial and lateral collateral ligaments in tension.

SUMMARY OF MY INVENTION

I have invented a bicompartmental tensiometer for use in prosthetic knee surgery, and in particular for use in revision knee surgery. The tensiometer of my invention comprises two parallel, independently operable jaws which are inserted between the distal femur resection and the proximal tibia resection. The jaws are placed adjacent these resected surfaces and opened manually by the surgeon until the proper tension is placed on the collateral ligaments. Each of the jaws comprises two paddles which remain parallel to each other as they are opened. Moreover, the two paddles remain parallel to each other, or in the same angular orientation when adjusted, as placed adjacent the resected surfaces. Each jaw is held open by a pawl which engages a rack. With both sides of the knee joint simultaneously under appropriate tension, a more accurate evaluation of the anatomic alignment of the joint, due to the proper balancing of the collateral ligaments, can be made. It is at this point, also, that cutting jigs or blocks, such as a femoral anterior/posterior chamfer cutting block available from Intermedics Orthopedics, Inc., the Assignee of my invention, can be properly aligned with the knee joint while in flexion. This block may be drilled and pinned into place while the tensiometer is in operation. The tensiometer can then be removed prior to the use of a saggital saw with the cutting block.

With the foregoing in mind, it is a principle object of my invention to provide a tensiometer for knee surgery which operates simultaneously on both the medial and lateral compartments of the knee joint.

It is a further object of my invention to provide such a tensiometer which can be used with either the right or left knee.

It is an object of my invention to provide a tensiometer in which two paddles, comprising a jaw, remain parallel when moved.

Another object of my invention is to provide a bicondylar tensiometer which operates independently on each condyle, and in which both jaws and paddies forming the jaws move in parallel fashion with respect to their co-operating parts.

These and other objects and features of my invention will be apparent from the following detailed description taken with respect to the accompanying drawings.

DETAILED DESCRIPTION OF MY PREFERRED EMBODIMENT

Figure 1:
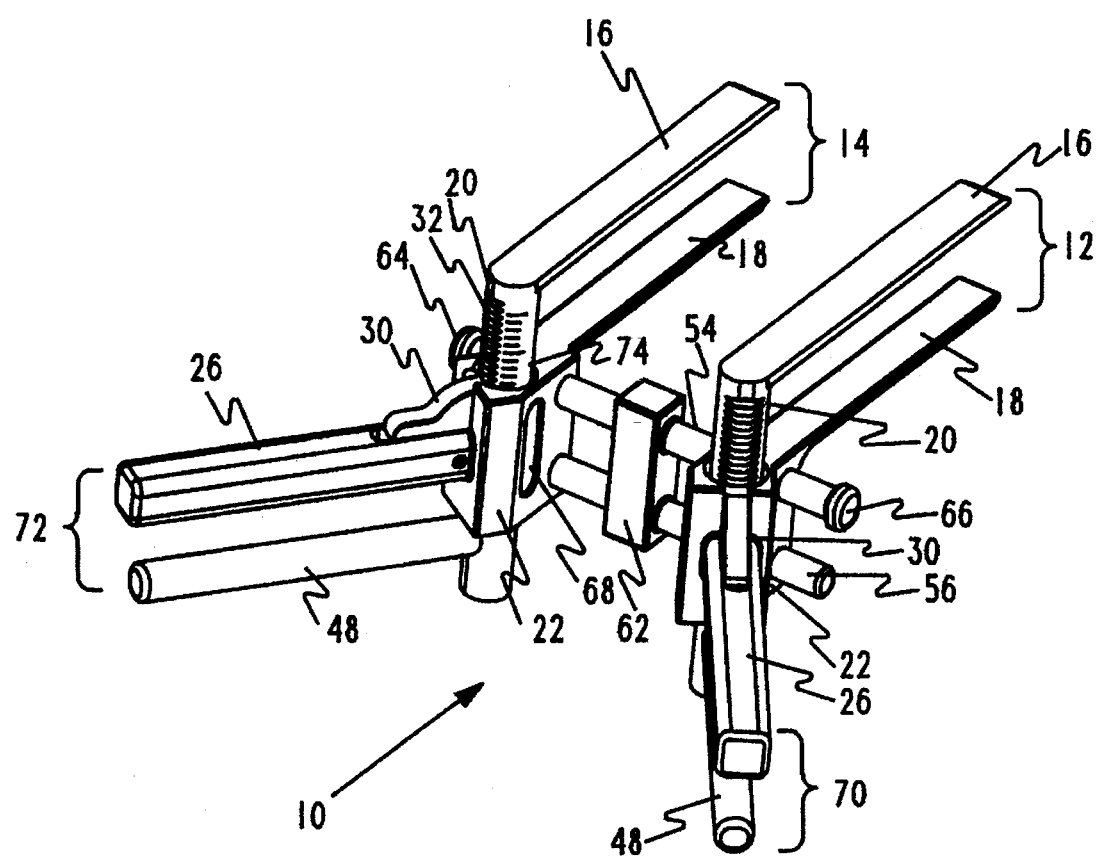
FIG. 1 is a perspective view of a bicompartmental tensiometer in accordance with my invention.
Figure 2:
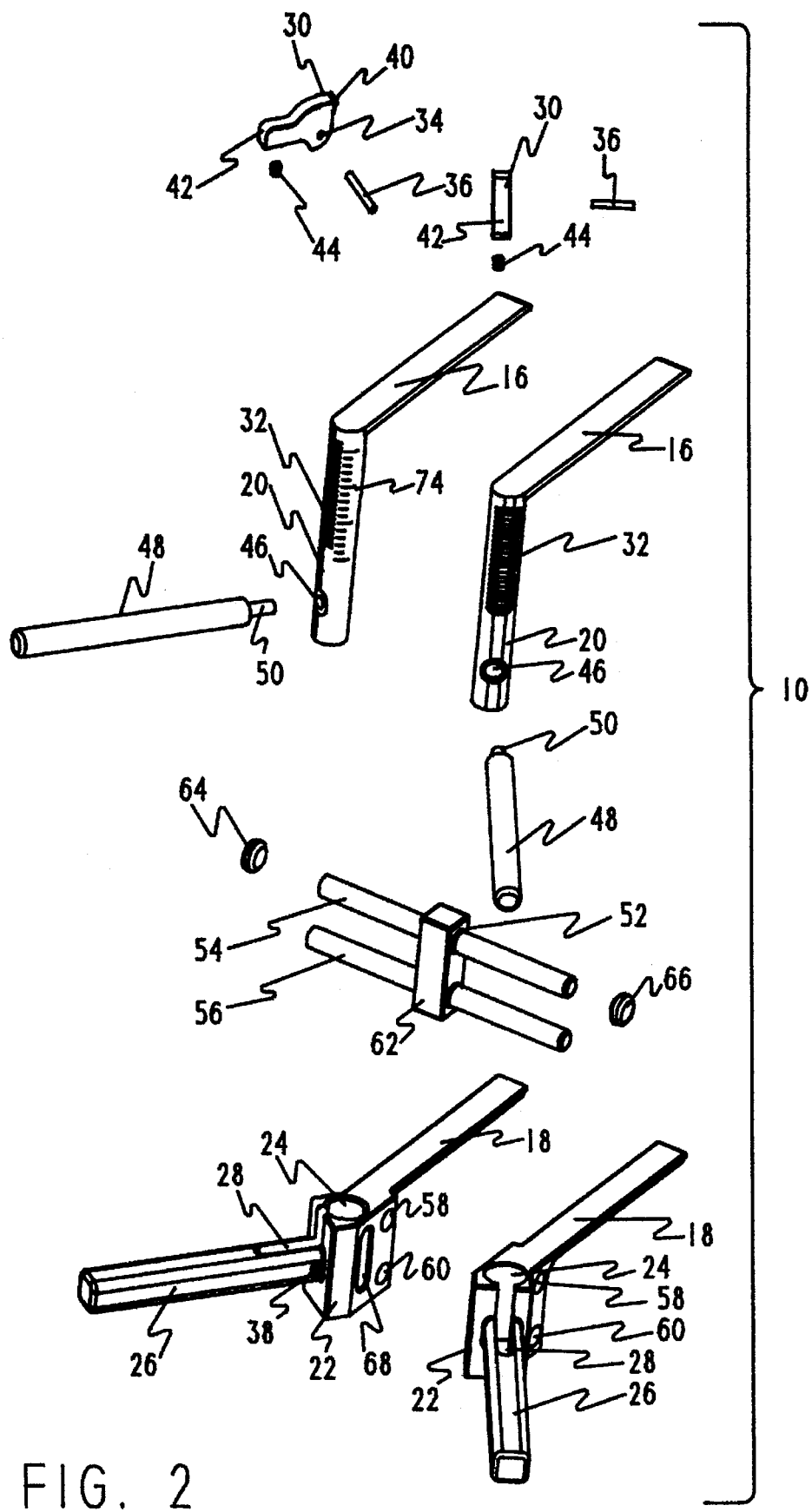
FIG. 2 is an exploded perspective view of the tensiometer of FIG. 1.

I will now describe my invention with respect to the accompanying drawings. Like numerals will refer to like parts throughout all the drawings. A bicompartmental tensiometer, generally designated 10, for use in knee surgery is illustrated in perspective view in FIG. 1. The tensiometer 10 can be used on either a patient's right knee or on the left knee. I will, therefore, describe my invention from the perspective of the surgeon utilizing the apparatus, such that "right" refers to the right hand side of the surgeon manipulating the apparatus, while "left" refers to the left hand side of the surgeon.

The tensiometer 10 comprises two jaws, a right jaw 12 and a left jaw 14. The jaws are initially closed and are slid between a resected surface on the distal end of the patient's femur and a resected surface on the proximal end of the patient's tibia, usually at the medial and lateral ends of these resected surfaces. The jaws 12, 14 are first adjusted to be accurately placed into these positions and then opened independently to place the collateral ligaments of the knee in tension. The patient's knee may be either in extension or flexion, and it is usual for a surgeon to observe the action of the knee joint in both positions. Each jaw 12, 14, comprises an upper paddle 16 and a lower paddle 18. Preferably, the paddles 16, 18, are flat with rounded or chamfered corners. The upper paddles 16 are each connected to a shaft 20 at a right angle. Each lower paddle 18 is connected to a body 22. Each body 22 has its longest dimension parallel to the shaft 20 of its associated upper paddle 16, and has a through bore forming a bearing 24 for the shaft 20. Each shaft 20 rides in its associated bearing 24, so that the upper and lower paddles 16, 18 can be displaced with respect to each other. The upper and lower paddles 16, 18 have a specific angular orientation with respect to each other. In my preferred embodiment, the two paddles are parallel, but other angular orientations could be chosen. When the two paddles are displaced with respect to each other, however, they retain the same angular orientation. That is, each part of the upper paddles in contact with bone would move the same distance with respect to a corresponding part of the lower paddle. I call this motion "parallel motion".

Each body 22 has a handle 26 extending therefrom. A slot 28 extends partially through the handle adjacent the body 22 and into the body 22, opening into the bearing 24. This slot 28 receives a pawl 30. Each pawl 30 engages a rack 32 on its respective shaft 20. Each pawl comprises a pivot 34 through which is passed a pin 36. Each pin 36 also engages a pivot bore 38 in its respective handle. A tooth 40 engages the rack 32 to prevent the jaws 12, 14 from closing. A trigger 42 permits the surgeon to disengage the pawl 30 from the rack 32 and close the respective jaw. A spring 44 is placed within each pawl slot 28 under the respective trigger 42 to urge the pawl against the rack.

Distally from its respective upper paddle 16, each shaft 20 has a threaded stopped bore 46. A grip lever 48 is inserted into each threaded stopped bore 46 such that a threaded shaft 50 thereon can be screwed into the stopped bore 46. When assembled, the upper paddle on the right will be over and parallel to the lower paddle on the right and will be parallel both to the upper paddle on the left and to the lower paddle on the left. The handle 26 on the right side will be parallel to its associated grip lever 48 and the handle of the left side will be parallel to its associated grip lever. Preferably, the two jaws 12, 14 are parallel to one another, but the right and left handles will diverge from their respective bodies away from each other. This provides greater room for the physician to manipulate the jaws simultaneously.

The right and left jaws 12, 14 are held parallel to one another by a stabilizer assembly 52. The stabilizer assembly 52 comprises an upper support rod 54 and a lower support rod 56. These support rods 54, 56 pass through bores 58, 60 in each body 22. The two rods 54, 56 are held in rigid planar relationship to each other by a brace 62 into which the rods 54, 56 are inserted and then secured by welding. Caps 64, 66 may be placed on the ends of one or both support rods to prevent the bodies 22 from sliding completely off the rods. As an additional feature, the bodies 22 may be provided with sterilization slots, such as slot 68, both to reduce the weight of the tensiometer 10 and to provide better sterilization for the instrument.

In use, the jaws 12, 14 are closed by opening the pawl 30 and moving the respective grip lever 48 away from its associated handle 26. The handle 26 and grip lever 48 on the right side form a grip assembly 70 for manipulating the right jaw 12, while the handle 26 and grip lever 48 on the left side form a left grip assembly 72 for manipulating the left jaw 14. With the jaws 12, 14 closed, the paddles 16, 18 may be inserted between a resected surface on the distal end of the femur and a resected surface on the proximal end of the tibia. The jaws 12, 14 can then be positioned optimally under their respective condyles by sliding them outwardly or inwardly along the rods 54, 56 of the stabilizer assembly 52.

With the jaws 12, 14 in appropriate position between the patient's femur and tibia, the surgeon can then independently open the jaws by squeezing the right grip assembly 70 and the left grip assembly 72. As the grip assemblies 70, 72 close, their associated jaws 12, 14 open. The surgeon will be able to manually detect the resistance. When the appropriate tension has been achieved, the associated pawl 30 will automatically engage the rack 32, due to the spring tension on each pawl 30, supplied by spring 44, and hold the knee open at the selected tension. The pawl 30 need not be depressed while operating the grip assemblies 70, 72. While the grip assemblies are in operation, the pawl 30 will pivot, at point 34 such that the pawl 30 tip will be forced open, due to the shape of teeth on the rack 32, and act as a ratchet type mechanism for the full length of engagement with the teeth on the rack. Because the spring 44 loads the pawl 30 in the forward direction into the teeth on the rack 32 the pawl tip can continually engage the rack teeth. With the collateral ligaments under the surgeon's selected tension, appropriate measurements can be made to select the size of the prosthesis to be implanted and to place and make the necessary resecting cuts. Depending on the type of prosthesis selected by the surgeon, other measurement instruments may be employed. However, a scale 74 may also be provided along each shaft 20 so that the amount by which each condyle has been spread by the tensiometer 10 can be measured directly.

My invention may be embodied in other specific forms without departing from the teachings thereof. The foregoing description is to be considered in all respects to be illustrative and not restrictive. The scope of my invention is defined by the following claims, and all changes which come within the scope of equivalency of the claims are intended to be encompassed therein.

I claim as my invention:

1. A surgical apparatus for spreading a distal end of a femur away from a proximal end of a tibia at a knee joint of a patient thereby placing adjacent collateral ligaments in tension, said apparatus comprising means for spreading a medial side of said knee, means for spreading a lateral side of said knee, and a pair of parallel rods connecting said means for spreading said medial side and said means for spreading said lateral side for holding said means for spreading in selectable non-rotatable spaced relation with respect to each other, each rod slidingly received in at least one of said means for spreading.

2. The surgical apparatus according to claim 1 wherein at least one of said means for spreading comprise an upper paddle, a lower paddle, means for adjusting the position of said paddles relative to each other, and means for locking said adjusting means to retain said upper and lower paddles in a selected position relative to each other.

3. The apparatus according to claim 2 wherein said means for adjusting comprise a shaft attached to said upper paddle, and body means attached to said lower paddle, said body means having a bore, said shaft being slidingly received in said bore, and wherein said means for locking comprise a rack affixed to said shaft, and a pawl attached to said body means, said pawl selectively engaging said rack.

4. The apparatus according to claim 1 wherein at least one of said means for spreading a side of a knee comprises an upper paddle, a lower paddle, and means for adjusting the position of said paddles relative to each other while permitting only parallel motion of said paddles.

5. The apparatus according to claim 4 wherein said means for adjusting comprise a shaft attached to said upper paddle, and body means attached to said lower paddle, said body means having a bore, said shaft being slidingly received in said bore.

6. The apparatus according to claim 5 further comprising means for measuring displacement of said upper paddle with respect to said lower paddle.

7. The apparatus according to claim 6 wherein said means for measuring comprises a scale on said shaft.

8. A surgical apparatus for spreading a distal end of a femur away from a proximal end of a tibia at a knee joint of a patient thereby placing adjacent collateral ligaments in tension, said apparatus comprising means for spreading a medial side of said knee, said means for spreading said medial side of said knee having a medial upper paddle, and a medial lower paddle, and means for adjusting the position of said medial paddles relative to each other while permitting only parallel motion of said paddles, means for spreading a lateral side of said knee, said means for spreading said lateral side of said knee having a lateral upper paddle, and a lateral lower paddle, and means for adjusting the position of said lateral paddles relative to each other while permitting only parallel motion of said paddles, and means for non-rotatably translating in the medial-lateral direction said means for spreading said medial side of said knee away from or towards said means for spreading said lateral side of said knee.

9. The apparatus according to claim 8 further comprising means for locking said adjusting means to retain said upper and lower paddles in a selected position relative to each other.

10. The apparatus according to claim 9 wherein said means for locking comprise a rack affixed to said shaft, and a pawl attached to said body means, said pawl selectively engaging said rack.

11. The apparatus according to claim 8 wherein said means for adjusting comprise a shaft attached to said upper paddle, and body means attached to said lower paddle, said body means having a bore, said shaft being slidingly received in said bore.

12. The apparatus according to claim 11 further comprising means for measuring displacement of said upper paddle with respect to said lower paddle.

13. The apparatus according to claim 12 wherein said means for measuring comprises a scale on said shaft.

* * * * *